(12) United States Patent
Mundt et al.

(10) Patent No.: US 9,057,370 B2
(45) Date of Patent: Jun. 16, 2015

(54) NEGATIVE DEAD VOLUME SYRINGE

(75) Inventors: Jason B. Mundt, Sparks, NV (US); Stephen E. Ewing, Reno, NV (US)

(73) Assignee: Hamilton Company, Reno, NV (US)

( * ) Notice: Subject to any disclaimer, the term of this patent is extended or adjusted under 35 U.S.C. 154(b) by 1098 days.

(21) Appl. No.: 12/228,002

(22) Filed: Aug. 8, 2008

(65) Prior Publication Data

US 2010/0034705 A1 Feb. 11, 2010

(51) Int. Cl.
| | |
|---|---|
| *B01L 3/00* | (2006.01) |
| *F04B 49/16* | (2006.01) |
| *A61M 5/142* | (2006.01) |
| *A61M 5/36* | (2006.01) |
| *F04B 53/14* | (2006.01) |
| *A61M 5/14* | (2006.01) |
| *A61M 5/315* | (2006.01) |

(52) U.S. Cl.
CPC ............ *F04B 49/16* (2013.01); *A61M 5/14216* (2013.01); *A61M 5/36* (2013.01); *A61M 2005/1402* (2013.01); *A61M 2005/31516* (2013.01); *F04B 53/14* (2013.01)

(58) Field of Classification Search
CPC ............ A61M 2005/1402; A61M 2005/31516
USPC .......... 422/501, 546, 500; 604/188, 187, 240; 73/864.87
See application file for complete search history.

(56) References Cited

U.S. PATENT DOCUMENTS

| | | | | |
|---|---|---|---|---|
| 2,230,654 | A * | 2/1941 | Plunkett | 526/255 |
| 3,581,956 | A * | 6/1971 | Reid | 222/386 |
| 5,188,601 | A * | 2/1993 | King | 604/110 |
| 6,972,008 | B2 | 12/2005 | Bills | |
| 2002/0077589 | A1* | 6/2002 | Tessari | 604/82 |
| 2007/0088289 | A1 | 4/2007 | Bargh | |

OTHER PUBLICATIONS

Pure & Appl. Chem., vol. 63, No. 12, pp. 1793-1804, 1991. Structure and Mechanical Properties of Ultra-High Molecular Weight Polyethylene Deformed Near Melting Temperature.*

* cited by examiner

*Primary Examiner* — Natalia Levkovich
(74) *Attorney, Agent, or Firm* — Dennis A. DeBoo; Audrey A. Millemann; Weintraub Tobin

(57) ABSTRACT

A negative dead volume syringe comprising a body defining a chamber, a syringe tip disposed at a distal end of the chamber and having a tip passageway therethrough in open communication with the chamber, a rod extending from a first end within the chamber to a second end coupleable to a motor to produce bidirectional motion of the rod, and a plunger tip having a proximal portion coupled to the first end of the rod, a medial portion distally extending from said proximal portion and shaped to complement the tip passageway, and a tip extension distally extending from said medial portion and shaped to be received within a dead volume defined by a passageway of a valve coupleable to the syringe tip wherein the plunger tip ensures evacuation of fluid and air from the chamber, syringe tip, and dead volume of the valve upon distal displacement of the rod.

35 Claims, 13 Drawing Sheets

NEGATIVE DEAD VOLUME SYRINGE

FIELD OF THE INVENTION

This invention relates generally to syringes and, in particular, to a negative dead volume syringe for use with a syringe pump.

BACKGROUND OF THE INVENTION

A conventional syringe pump system for aspirating and dispensing volumes of liquid includes a syringe mounted vertically or horizontally on a syringe pump with a drive means detachable coupled to a plunger emanating from a bottom or rearward end of a chamber of the syringe and a rotary valve detachable coupled to a top or forward end of the syringe in open communication with the chamber.

The rotary valve typically includes a stationary passageway in open communication with both the syringe chamber and a rotatable passageway extending through a rotatable valve member of the rotary valve for providing open communication between the syringe chamber and an inlet port of the valve or an outlet port of the valve as selected by the position of the rotatable valve member. An inlet fluid line typically couples the inlet port to a first reservoir of fluid while an outlet fluid line typically couples the outlet port to a second reservoir or a subsequent conventional syringe pump system for dispensing fluid thereto.

For aspirating fluid, the conventional syringe pump system rotates the rotatable valve member to provide open fluid communication between the syringe chamber and the first reservoir of fluid and then draws the plunger downward for aspirating fluid into the syringe chamber from the first reservoir of fluid. For dispensing fluid, the conventional syringe pump system rotates the rotatable valve member to provide open fluid communication between the syringe chamber and the second reservoir and then drives the plunger upward for dispensing fluid from the syringe chamber to the second reservoir or to the subsequent conventional syringe pump system thereby completing one syringe pump cycle.

Although the aim of mounting the syringe vertically is to help remove air from the syringe as air bubbles rise naturally towards the rotary valve during use, there is an inherent problem with the conventional syringe pump system in that the stationary passageway of the rotary valve creates and defines a dead volume in the system where air becomes trapped and unable to exit therefrom.

For example, when the plunger is at the top of its stroke, the air in the syringe is pushed into the dead volume defined by the stationary passageway and then when the syringe is refilled, because the refilling occurs through the same stationary passageway, the trapped air is pushed back into the syringe ahead of the inflowing fluid. As a result of the fact that the air is much more easily compressed than the liquid to be pumped, air bubbles in the syringe can cause the performance to be reduced to a level at which accuracy and reliability of pumping of the liquid is unacceptable.

In particular, each conventional syringe pump system undergoes an initialization process for priming the system which serves the purpose of completely filling the input fluid line up to the syringe with one or more user selected fluids. When the fluid first reaches the valve, the syringe draws in both fluid and air causing the fluid to foam or froth within the chamber of the syringe. Then, the rotatable valve member is turned and the plunger is actuated in an effort to dispense or push the fluid and air out of the outlet port of the valve. An impediment to this effort comes about as a result of the plunger pushing air from the syringe into the dead volume defined by the stationary passageway where it becomes trapped and unable to exit therefrom. Thus, when the valve member is turned back to communicate the syringe chamber with the first reservoir of fluid and the plunger is again actuated the air that was previously trapped in the dead volume is drawn back into the syringe ahead of the inflowing fluid thereby resulting in additional strokes for initially priming the conventional syringe pump system for obtaining a solid train of fluid flowing through the syringe. Hence, these additional strokes result in both time and fluid consumption which both can be costly and in short supply.

Another problem that is common in conventional syringe pump systems is the diminishing return or dilution over time during a purging process such as is associated with switching from a first fluid to a second different fluid.

For example, the purging process of the conventional syringe pump system includes aspirating or drawing both a first remaining fluid and a second different fluid into the syringe chamber where the fluids mix. Subsequently, this fluid mixture is dispensed out of the syringe by rotating the rotatable valve member to communicate the syringe chamber with the outlet port of the valve and then actuating the plunger for dispensing the fluid mixture out of the outlet port. Although fluid mixture is dispensed from the outlet port of the valve, a portion of the fluid mixture remains trapped within the dead volume of the valve defined by the stationary passageway. Thus, when the rotatable valve member is turned back to communicate the syringe chamber with the inlet port of the valve both the fluid mix remaining within the dead volume of the valve and fluid in the inlet fluid line is aspirated into the syringe chamber thereby having a diminishing return or dilution of the fluid drawn from the inlet fluid line. Hence, this results in the need for additional strokes for purging the conventional syringe pump system of fluid thereby resulting in both time and fluid consumption which both can be costly and in short supply.

A further problem associated with conventional syringe pump systems is with respect to the out gassing that is linked with running fluids through conventional syringe pump systems.

Particularly, a user fluid that is ran through the conventional syringe pump system has a small amount of gas that can degas and turn into bubbles because, by its nature, the syringe in the syringe pump system is reducing and pressurizing the fluid. When the pressure on the fluid is reduced, the bubbles out gas and turn into bubbles that tend to stay in the syringe or dead volume of the valve and stubbornly stick to the sides thereof.

The significant shortcomings as described above also apply to valves that employ a method of switching or opening and closing flow paths inside of the valve by means other than a rotary action.

Moreover, an additional dead volume contributing to the problems described above may be found in the tip of the conventional syringe.

Hence, there is a need to overcome the significant shortcomings of the known prior-art as delineated hereinabove.

BRIEF SUMMARY OF THE INVENTION

Accordingly, and in one aspect, an embodiment of the invention ameliorates or overcomes one or more of the shortcomings of the know prior art by providing a negative dead volume syringe that eliminates syringe dead volume and that subtracts or directly displaces dead volume from a valve coupled to the syringe thereby resulting in a syringe pump system that provides faster, more reliable system priming and purging with less fluid loss and that increases the efficiency in forcing air including bubbles out of the syringe and coupled valve during system operation.

In particular, an embodiment of the invention provides a negative dead volume syringe for repetitively aspirating and dispensing fluids in a fluid handling system, the negative dead volume syringe comprising: an elongated body defining a chamber for retaining fluid and having an open proximal end and a distal end; a syringe tip extending from the distal end and having a syringe tip passageway therethrough in fluid communication with the chamber; an elongated plunger rod extending proximally from a distal end of the plunger rod disposed within the elongated body and through the open proximal end of the elongated body to a proximal end of the plunger rod removeably coupleable to a syringe pump motor to produce bidirectional linear displacement of the plunger rod; and a plunger tip comprising a proximal plunger tip portion coupled to the distal end of the plunger rod, a medial plunger tip portion distally extending from said proximal plunger tip portion and shaped to complement the syringe tip passageway, and a distal plunger tip portion or nubbin distally extending from said medial plunger tip portion and sized to extend beyond the syringe tip and shaped to be complementally received within and substantially or completely fill a valve dead volume defined by a stationary passageway of a rotary valve coupleable to the syringe tip so that the plunger tip ensures completer or substantially complete dispensing of fluid from the chamber while reducing bubble formation and facilitating bubble removal from the chamber, from the syringe tip passageway, and from the valve dead volume upon distal displacement of the plunger rod and the plunger tip coupled thereto.

Additionally, and in one embodiment, the plunger tip of the negative dead volume syringe is integrally formed as a single device or monolith of material comprising: a cylindrically shaped proximal plunger tip portion coupled to the distal end of the plunger rod and comprising at least one externally circumscribing seal or rib configured to slideably engage the interior surface of the chamber for providing a tight, leak-free seal between the plunger tip and the chamber; a frusto-conically shaped medial plunger tip portion distally extending from said proximal plunger tip portion and shaped to slideably and conformingly engage a frusto-conically shaped void defining the passageway of the syringe tip; and a cylindrically shaped or slightly tapering distal plunger tip portion or nubbin sized to extend beyond the syringe tip and shaped to be complementally received within and substantially fill the valve dead volume defined by the stationary passageway of the rotary valve so that the plunger tip ensures completer or substantially complete dispensing of fluid from the chamber while reducing bubble formation and facilitating bubble removal from the chamber, from the passageway of the syringe tip, and from the valve dead volume upon distal displacement of the elongated plunger rod and the plunger tip coupled thereto.

Furthermore, and in another embodiment, the plunger tip of the negative dead volume syringe is integrally formed as a single device or monolith of material comprising: a cylindrical or slightly tapering proximal plunger tip portion coupled to the distal end of the plunger rod; a cylindrical or slightly tapering medial plunger tip portion distally extending from said proximal plunger tip portion and shaped complemental to the syringe tip passageway; and a cylindrical or slightly tapering distal plunger tip portion or nubbin sized to extend beyond the syringe tip and shaped to be complementally received within and substantially fill the valve dead volume defined by the stationary passageway of the rotary valve so that the plunger tip ensures complete or substantially complete dispensing of fluid from the chamber while reducing bubble formation and facilitating bubble removal from the chamber, from the passageway of the syringe tip, and from the valve dead volume upon distal displacement of the elongated plunger rod and the plunger tip coupled thereto.

Accordingly, and in one aspect, an embodiment of the invention provides a negative dead volume syringe for a syringe pump system that is comprised of a plunger tip that substantially removes all dead volume from or provides zero dead volume in the chamber and tip of the syringe and that subtracts or displaces dead volume from a rotary valve coupled to the syringe.

In another aspect, an embodiment of the invention provides a negative dead volume syringe for a syringe pump system that is comprised of a plunger tip that allows quicker priming times due to removal of syringe and valve dead volume which results in fewer priming strokes and less working fluid loss as compared to a conventional syringe pump system.

In another aspect, an embodiment of the invention provides a negative dead volume syringe for a syringe pump system that is comprised of a plunger tip that provides a transition zone that causes less cavitation during priming.

In another aspect, an embodiment of the invention provides a negative dead volume syringe for a syringe pump system that is comprised of a plunger tip that eliminates or reduces dead volume in a chamber of the syringe, in a tip of the syringe, and in a valve coupled to the tip of the syringe thereby clearing out fluid mixtures from this dead volume on each stroke so that the fluid mixture is not drawn back into the syringe thereby eliminating the known prior art problem of the diminishing return or dilution on subsequent aspiration strokes and thus, decreasing the number of strokes, the time, the wasted fluid, and the associated costs required to purge one fluid when changing over to another.

In another aspect, an embodiment of the invention provides a negative dead volume syringe for a syringe pump system that is comprised of a plunger tip that reduces bubble formation and that facilitates bubble removal from the plunger tip surface resulting from cavitation and out gassing of bubbles during continuous syringe pump system use thereby precluding the bubbles from creating an air spring in the system and degrading accuracy.

In another aspect, an embodiment of the invention provides a negative dead volume syringe for a syringe pump system that is comprised of a plunger tip that increases fluid velocity at the end of syringe dispensing strokes thereby allowing quicker priming, running, and purging times.

In another aspect, an embodiment of the invention provides a negative dead volume syringe for a syringe pump system that is comprised of a plunger tip comprising a distal extension or nubbin portion which is formed from the same material as the remainder of the plunger tip so as not to introduce a different or additional material into the fluid path.

Accordingly, it should be apparent that numerous modifications and adaptations may be resorted to without departing from the scope and fair meaning of the claims as set forth hereinbelow following the detailed description of the invention.

DETAILED DESCRIPTION OF THE INVENTION

Figure 1:
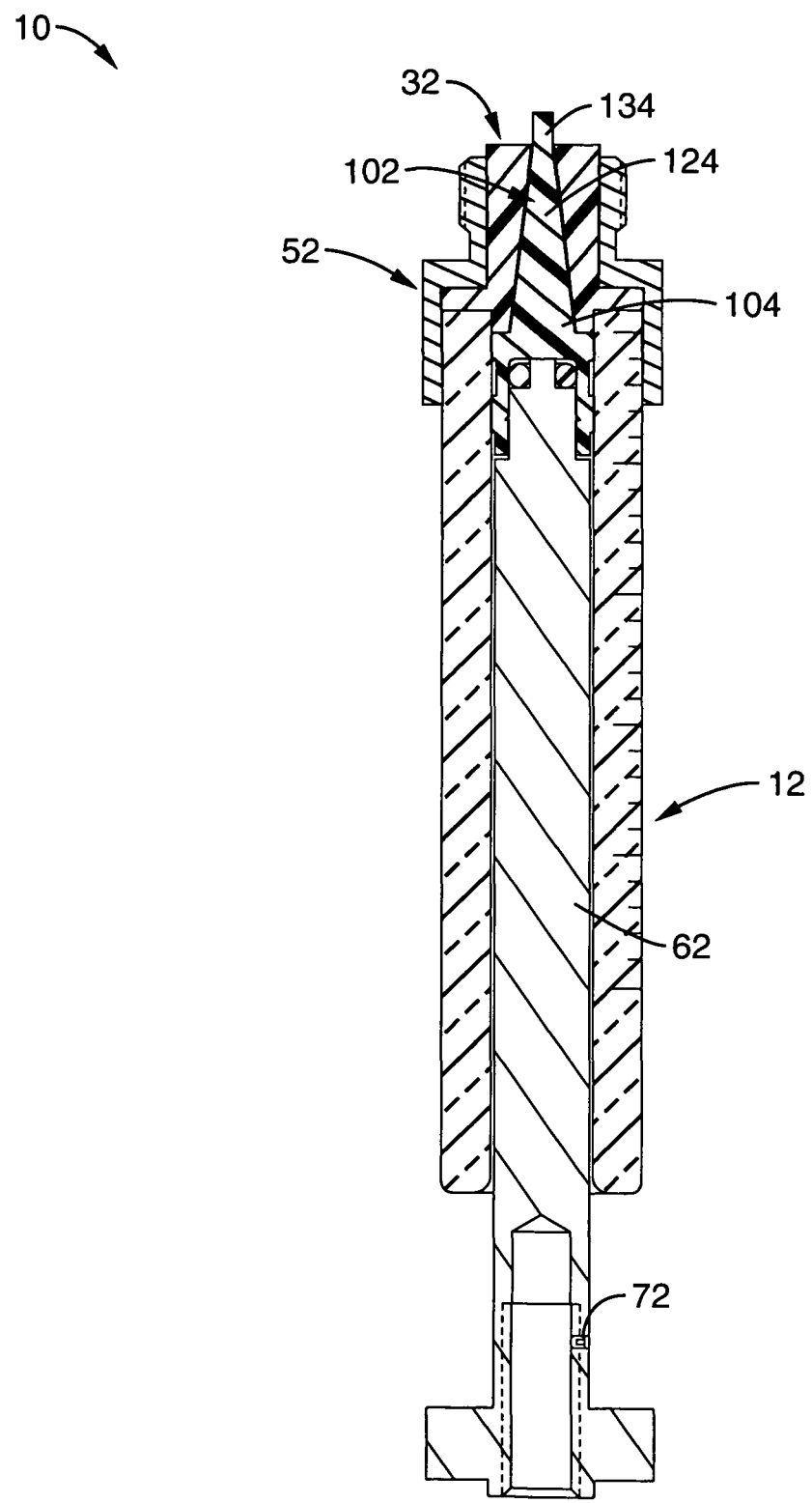
FIG. 1 is a sectional view of an embodiment of a negative dead volume syringe.
Figure 2:
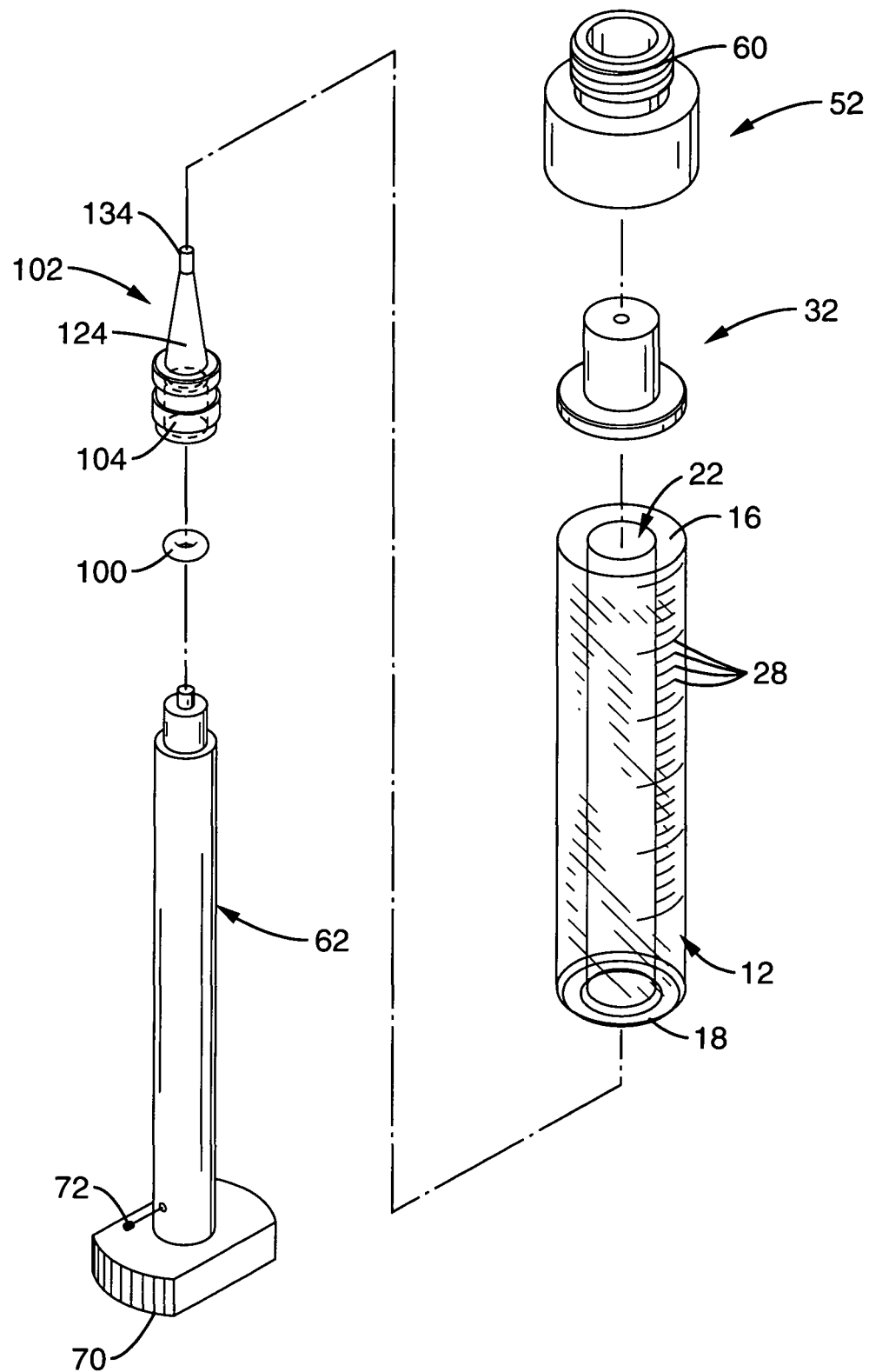
FIG. 2 is an exploded parts view of the negative dead volume syringe illustrated in FIG. 1.

Considering the drawings, wherein like reference numerals denote like parts throughout the various drawing figures, reference numeral 10 is directed to a negative dead volume syringe according to an embodiment of the present invention.

Referring to FIG. 1, and in one embodiment, the negative dead volume syringe 10 is comprised of a syringe body or barrel 12, a syringe tip 32, a multi-diameter hub 52, a linearly reciprocable plunger 62, and a plunger tip 102.

Syringe Body or Barrel 12

Referring now to FIGS. 1 through 4, the syringe body or barrel 12 of the negative dead volume syringe 10 is comprised of a cylindrical sidewall 14 axially-extending between an open distal (front) end 16 and an open proximal (rear) end 18 of the barrel 12. The cylindrical sidewall 14 includes an interior surface 20 that defines an open ended bore or chamber 22 axially extending through the barrel 12 between the open distal end 16 and the open proximal end 18 of the barrel 12.

Additionally, an exterior slightly radially extending annular lip 26 proximally transitions from the cylindrical sidewall 14 at a location adjacent the open proximal end 18 of the barrel 12. The barrel 12 is typically constructed of, but not limited to, a glass or a transparent plastic material and optionally has graduations 28 on its side.

Syringe Tip 32

Still referring to FIGS. 1 through 4, the syringe 10 further comprises the syringe tip or insert 32 which is comprised of a first abbreviated cylindrical section 34 disposed through the open distal end 16 and closely fitted within the chamber 22 of the barrel 12.

Additionally, the abbreviated cylindrical section 34 extends from an annular rear face 36 within the chamber 22 to a radially extending flange 38 abutting against a distal end 30 of the cylindrical sidewall 14 of the barrel 12. In turn, the radially extending flange 38 transitions into a second cylindrical section 40 extending from the flange 38 and terminating to a substantially flat annular front face or sealing surface 42 of the syringe tip 32.

Furthermore, the syringe tip 32 includes a distally-facing frusto-conically shaped inner surface 44 extending through the syringe tip 32 for defining an open ended frusto-conically shaped void or passageway 46 in fluid communication with the chamber 22 and tapering from an open rear end 48 to a front opening or orifice 50 in the sealing surface 42 of the syringe tip 32.

Moreover, and in one embodiment, the syringe tip 32 is an integrally formed one piece device made of, but not limited to, polytetrafluoroethylene (PTFE) material by, but not limited to, precision-machining and/or molding. Alternatively, the syringe tip 32 can be made of, but not limited to, a durable ultra-high molecular weight polyethylene (UHMWPE) by, but not limited to, precision-machining and/or molding. Ultra-high molecular weight polyethylene is a harder material than PTFE.

Hub 52

Continuing to refer to FIGS. 1 through 4, the syringe 10 further comprises the multi-diameter hub 52 which is comprised of an outer skirt portion 54 which circumscribes a distal portion of the barrel 12 and is adhered thereto. The outer skirt portion 54 also circumscribes the radially extending flange 38 of syringe tip 32. After circumscribing flange 38, the outer skirt portion 54 forwardly extends and perpendicularly transitions inwardly to a front annular portion 56 which radially extends inwardly along an outer surface of the radially extending flange 38 and terminates to a landing 58 of the hub 52 thereby defining a step down between the outer skirt portion 54 and the landing 58. In turn, landing 58 circumscribes the second cylindrical section 40 of the syringe tip 32 and briefly extends away from the radially extending flange 38 before stepping up into an externally threaded forward end 60. The externally threaded forward end 60 linearly extends along and circumscribes the second cylindrical section 40 and terminates prior to reaching the sealing surface 42 of the syringe tip 32. Externally threaded forward end 60 is preferably dimensioned to cooperate and provide threaded engagement with a variety of commercially available standard pump valves such as is exemplified by multi-port rotary valve 152 shown in at least FIG. 5 and as will be delineated in detail hereinbelow.

In view of the foregoing, and as illustrated in at least FIGS. 1 through 4, the outer skirt portion 54 has a diameter greater than a diameter of the landing 58 and, in turn, the externally threaded forward end 60 has a diameter greater than the landing diameter and less than the outer skirt diameter thereby defining multiple diameters of the multi-diameter hub 52.

Additionally, and in one embodiment, the multi-diameter hub 52 is an integrally formed one piece device constructed of, but not limited to, a metal material such as nickel-plated brass.

Linearly Reciprocable Plunger 62

Continuing to refer to FIGS. 1 through 4, the syringe 10 further comprises the linearly reciprocable plunger 62 which is comprised of a plunger rod 64 extending between a distal end 66 disposed within the chamber 22 of the barrel 12 and a proximal end 68 disposed outside of the chamber 22 of the barrel 12.

A drive head 70 is attached to the proximal end 68 of the plunger rod 64 by means of a set screw 72 and includes a bore 74 extending therethrough and terminating in plunger rod 64 for receiving an internally threaded sleeve 76 for threadedly coupling the linearly reciprocable plunger 62 to a linearly reciprocable drive arm 182 of the syringe pump 150 as further delineated hereinbelow. In one embodiment, the drive head 70 is substantially rectangularly shaped and includes a pair of opposing straight sides and a pair of opposing curved sides all extending between a substantially flat front face and a substantially flat rear face.

At the distal end 66, the plunger rod 64 transitions into a first annular shoulder 90 radially extending inwardly to a first radially reduced center post 92 distally extending away from the first annular shoulder 90. Similarly, a distal end of the first radially reduced center post 92 transitions into a second annular shoulder 94 radially extending inwardly to a second radially reduced center post 96 distally extending away from the second annular shoulder 94 and terminating into a substantially flat circular front face 98.

A ring seal 100 is received over the second radially reduced elongated center post 96 and into an annular recess defined by the second annular shoulder 94 and the center post 96.

In one embodiment, the plunger rod 64 is an integrally formed one piece device constructed of, but not limited to, a metal material such as stainless steel. Additionally, and in one embodiment, the drive head 70 is an integrally formed one piece device constructed of, but not limited to, a metal material such as stainless steel. Furthermore, and in one embodiment, the ring seal 100 is an integrally formed one piece device constructed of, but not limited to, a durable rubber material.

Plunger Tip 102

Continuing to refer to FIGS. 1 through 4, the syringe 10 further comprises a plunger tip 102 comprising a proximal plunger tip portion 104, a medial plunger tip portion 124, and a distal plunger tip extension or nubbin 134.

Proximal Plunger Tip Portion 104

Figure 3:
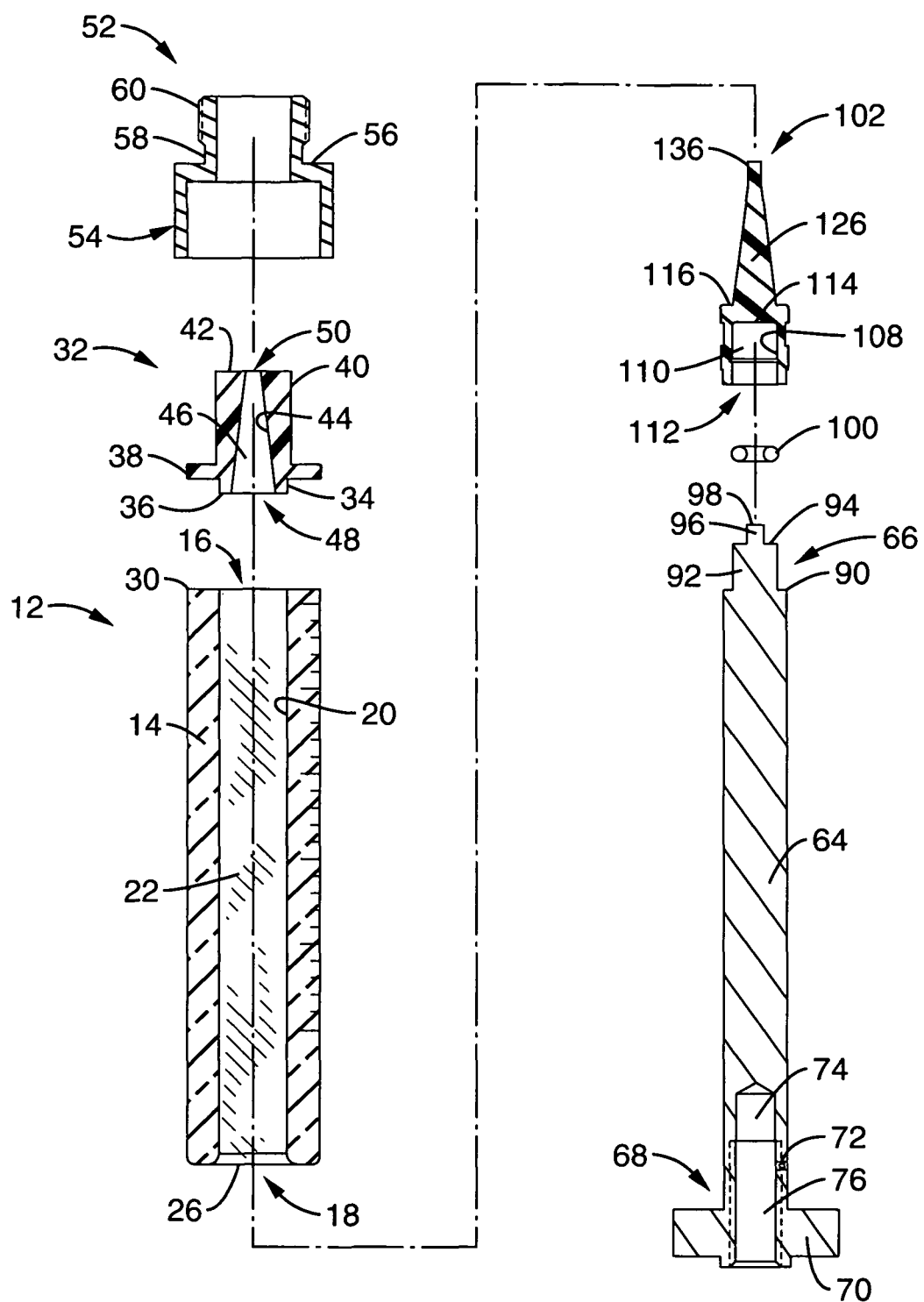
FIG. 3 is a sectional exploded parts view of the negative dead volume syringe illustrated in FIG. 1.
Figure 4:
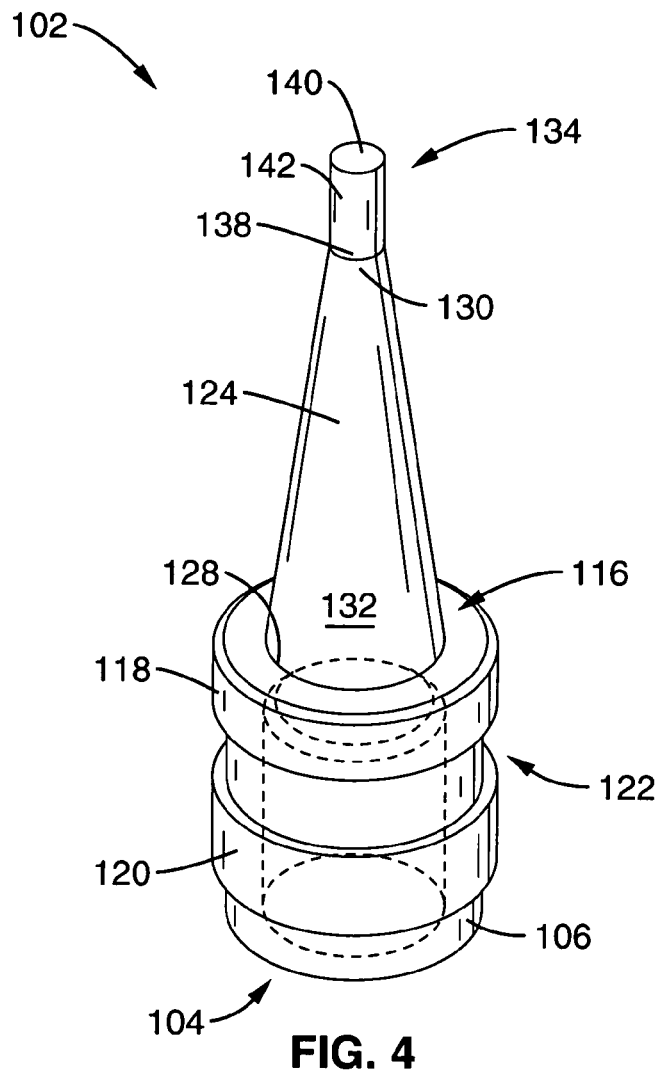
FIG. 4 is an enlarged perspective view of a plunger tip of the negative dead volume syringe illustrated in FIG. 1.
Figure 5:
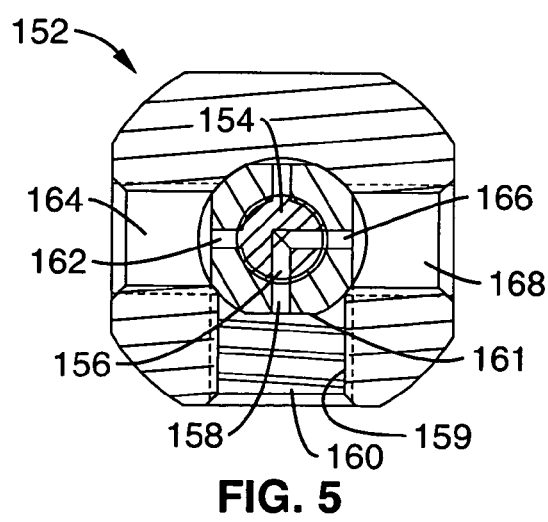
FIG. 5 is a sectional view of a multi-port rotary valve.
Figure 6:
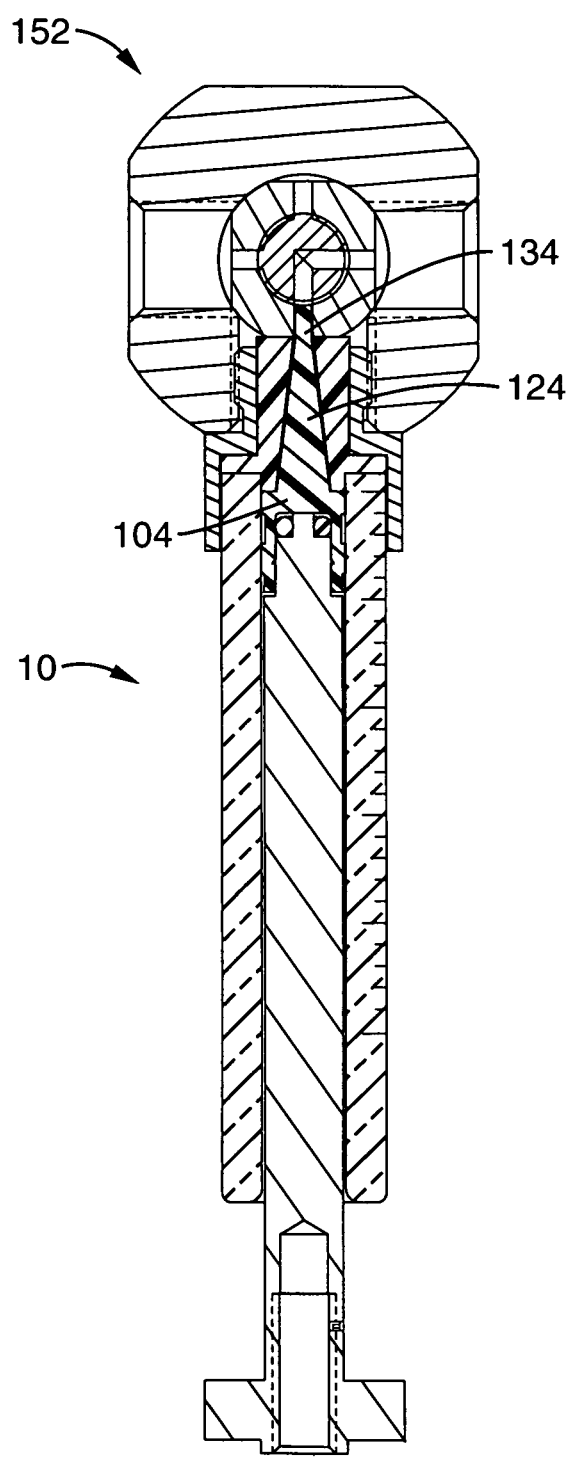
FIG. 6 is a sectional view of the negative dead volume syringe illustrated in FIG. 1 coupled to the multi-port rotary valve illustrated in FIG. 5.

As illustrated in FIGS. 3 and 4, and in one embodiment, the proximal plunger tip portion 104 includes an outer cylindrical wall 106 and an inner cylindrical wall 108. The inner cylindrical wall 108 defines a bore 110 extending from an open back end 112 to a closed forward end 114. The bore 110 being shaped for closely receiving the first radially reduced center post 92 of the plunger rod 64 and the second radially reduced center post 96 of the plunger rod 64 along with the circumscribing ring seal 100.

The outer cylindrical wall 106 of the proximal plunger tip portion 104 longitudinally extends from the open back end 112 to the closed forward end 114 were it transitions into a radially inwardly extending annular shoulder 116. The annular shoulder 116 abuts and seals against the annular rear face 36 of the syringe tip 32 upon full distal displacement of the elongated plunger rod 64.

A plurality of spaced apart collocated circumscribing seals or ribs 118, 120 are disposed on and preferably integrally formed with outer cylindrical wall 106. The seals 118, 120 are configured to slideably engage the interior surface 20 of the chamber 22 while providing a tight, leak-free seal between the plunger tip 102 and the interior surface 20 of the chamber 22. In one embodiment, seal 118 is disposed on the cylindrical wall 106 at a location immediately adjacent annular shoulder 116 and a space 122 separates seal 118 form seal 120. Accordingly, seal 118 and annular shoulder 116 abut and seal against the annular rear face 36 of the syringe tip 32 upon full distal displacement of the elongated plunger rod 64. Hence, the configuration of the proximal plunger tip portion 104 ensures complete or substantially complete dispensing of fluid from the chamber while facilitating bubble removal therefrom.

Although the present embodiment illustrates two seals 118, 120, the plunger tip 102 can also be fitted with a single seal or with more than two seals.

Additionally, the dual spaced apart seals 118, 120 enhance the axial alignment and stability of the plunger tip 102 and the plunger rod 64 within the chamber 22 of the barrel 12 as the linearly reciprocable plunger 62 is reciprocated up and down or back and forth during repetitive pump cycles. Hence, the dual spaced apart seals 118, 120 provide support along a longitudinal axis of the syringe thereby precluding rocking of the linearly reciprocable plunger 62 which might result in fluid leakage around and/or uneven wear of the seals 118, 120.

Furthermore, the circumscribing ring seal 100 applies a force against the inner cylindrical wall 108 of the proximal plunger tip portion 104 which results in energizing the seals 118, 120 against interior surface 20 of the chamber 22 of the barrel 12 thereby retaining the tight, leak-free seal between the plunger tip 102 and the interior surface 20 of the chamber 22 as the seals 118, 120 of plunger tip 102 wear.

Medial Plunger Tip Portion/Frusto-Conical Plunger Tip Portion 124

As noted hereinabove, the plunger tip 102 further comprises medial plunger tip portion 124 which is preferably integrally formed with the proximal plunger tip portion 104 and distally extends therefrom. In one embodiment, the medial plunger tip portion 124 is comprised of a solid and continuously tapering cross sectional area 126 extending from a base portion 128 integrally formed with the annular shoulder 116 of the proximal plunger tip portion 104 to a front portion 130 thereby defining a frusto-conically shaped medial plunger tip portion 124 having an outer frusto-conical surface 132.

The frusto-conically shaped medial plunger tip portion 124 is complementally shaped to slideably fill the frusto-conically shaped passageway 46 of the syringe tip 32 and the outer frusto-conical surface 132 is complementally shaped to slideably and conformingly engage the frusto-conically shaped inner surface 44 defining passageway 46 of the syringe tip 32 to ensure complete or substantially complete dispensing of fluid from the tip passageway 46 while facilitating bubble removal therefrom.

Distal Plunger Tip Extension/Nubbin 134

As also noted hereinabove, the plunger tip 102 further comprises distal plunger tip extension or nubbin 134 which is preferably integrally formed with the medial plunger tip portion 124 and distally extends from the front portion 130 thereof. In one embodiment, the distal plunger tip extension 134 is comprised of a solid cylindrical or slightly distally tapering cross sectional area 136 extending from a bottom portion 138 integrally formed with the front portion 130 of the medial plunger tip portion 124 to a substantially flat apex portion 140 thereby defining a cylindrical or slightly tapering distal plunger tip extension 134 having an outer cylindrical or slightly distally tapering surface 142. Hence, the bottom portion 138 of the distal plunger tip extension 134 has a diameter less than the base portion 128 of the medial plunger tip portion which, in turn, has a diameter less than the proximal plunger tip portion 104.

The distal plunger tip extension 134 is complementally shaped to substantially or completely fill a dead volume defined by a stationary passageway 158 of the valve 152 as further delineated hereinbelow by passing through and distally extending beyond the front orifice 50 of the syringe tip 32 to ensure complete or substantially complete dispensing of fluid from the dead volume 158 of the valve 152 while facilitating bubble removal therefrom. Hence, distal plunger tip extension 134 subtracts or displaces dead volume 158 from the valve 152 thereby defining a negative dead volume.

Accordingly, the distal plunger tip extension 134 can take on a large variety of different geometries wherein each of the geometries is preferably shaped complemental to a dead volume being filled in a substantial or complete manner. Additionally, the distal plunger tip portion or nubbin 134 can take on a large variety of different geometries that are not complemental to the dead volume being filled thereby resulting in a lesser degree of efficiency in solving the problems associated with the known prior art as delineated hereinabove in the background of the invention.

In one embodiment, the plunger tip 102 is an integrally formed one piece device or monolith of material made of, but not limited to, polytetrafluoroethylene (PTFE) by, but not limited to, precision-machining and/or molding. Alternatively, the plunger tip 102 can be made of, but not limited to, a durable ultra-high molecular weight polyethylene (UHM-WPE) material by, but not limited to, precision-machining and/or molding. Ultra-high molecular weight polyethylene is a harder material than PTFE.

Alternatively, the plunger tip extension can be coupled to the medial plunger tip portion 124 by being adhered to the medial plunger tip portion 124, by being screwed into the medial plunger tip portion 124, by being pressed into the medial plunger tip portion 124, being staked into the medial plunger tip portion 124, and/or by another coupling method. These and other methods also extend themselves to the coupling of the medial plunger tip portion 124 to the proximal plunger tip portion 104.

Syringe Pump 150 and Multi-Port Rotary Valve 152

The negative dead volume syringe 10 can be employed with a conventional syringe pump employing a conventional multi-port rotary valve for accurately and precisely aspirating and dispensing volumes of fluid. A variety of conventional syringe pumps and interchangeable multi port rotary valves are manufactured and sold by the assignee of the present patent application, Hamilton Company-USA, 4970 Energy Way, Reno, Nev. 89502.

Figure 7:
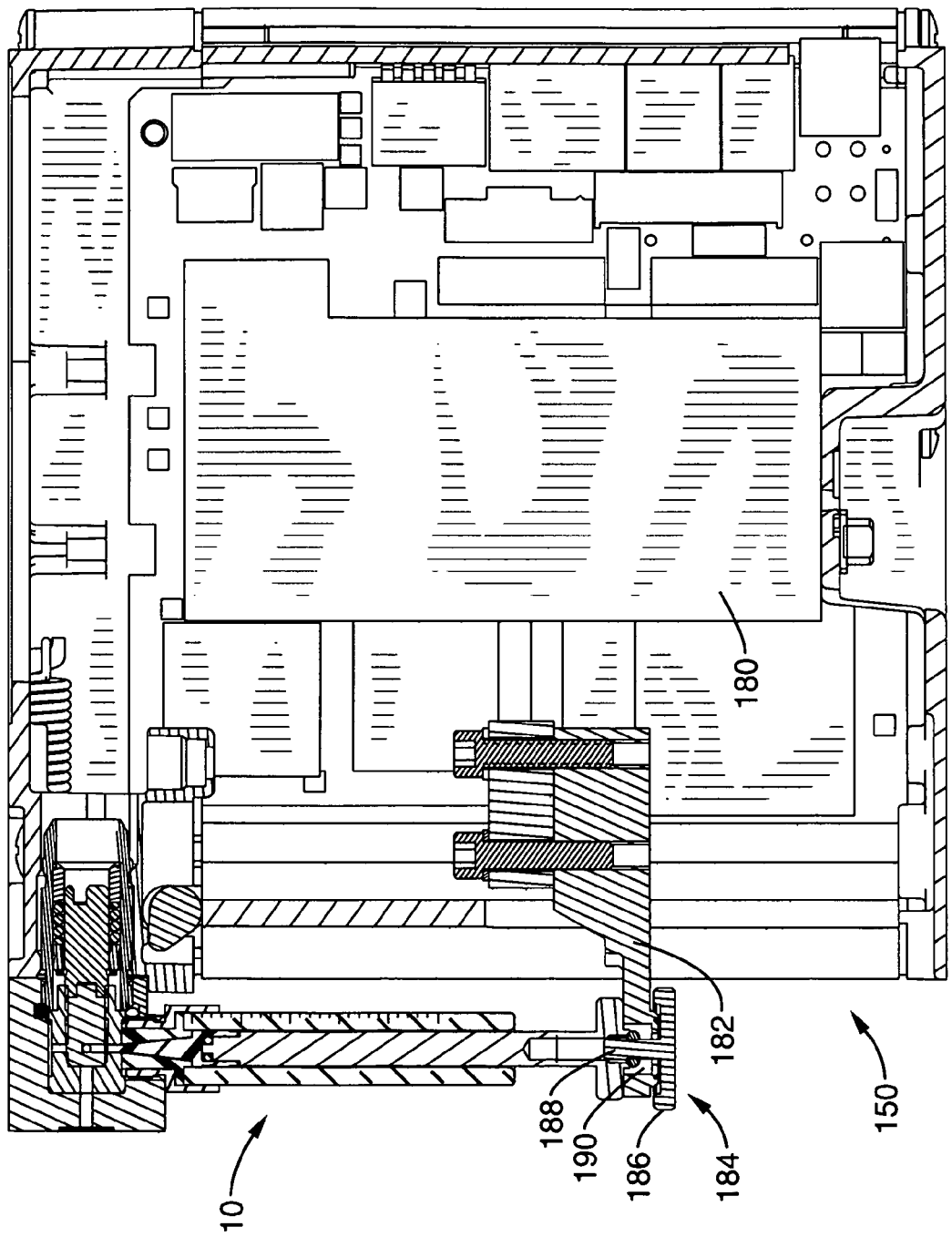
FIG. 7 is a sectional view of the negative dead volume syringe illustrated in FIG. 1 coupled to a syringe pump including the multi-port rotary valve illustrated in FIG. 5.

For example, and in one embodiment, FIG. 7 illustrates the negative dead volume syringe 10 vertically coupled in an easily detachable and in an operative manner with a Hamilton PSD/3 syringe pump 150 employing a Hamilton HV 3-2 multi-port rotary valve 152. Notwithstanding, the negative dead volume syringe 10 can also be coupled to a syringe pump that holds the syringe in a horizontal orientation. Furthermore, the negative dead volume syringe 10 can also be coupled to a syringe pump that holds the syringe in an oblique orientation. Moreover, the negative dead volume syringe 10 can be coupled in a vertical, horizontal, or oblique orientation to a variety of different syringe pumps at a location between, and in operative engagement with, a variety of different drives means employing different methods for driving the plunger 62 and a variety of different valves employing different methods for switching or opening and closing flow paths inside of the valve by means other than a rotary action.

Referring now to FIGS. 5 through 8, the multi-port rotary valve 152 is comprised of a rotatable valve member 154 having a passageway extending therethrough thereby defining a rotatable passageway 156. The multi-port rotary valve 152 is further comprised of a stationary passageway 158 that defines a valve dead volume and that is in open communication with a syringe receiving port 160 at one end and the rotatable passageway 156 at the other end. The syringe receiving port 160 includes an internally threaded section 159 for coupling the syringe 10 thereto for abutting the syringe tip sealing surface 42 against a sealing surface 161 of the syringe receiving port 160 by threadedly engaging the externally threaded forward end 60 of the hub 52 to the internally threaded section 159 in an easily detachable manner thereby providing open communication between the rotatable passageway 156, the stationary passageway or valve dead volume 158, the syringe tip passageway 46, and the chamber 22.

Additionally, the multi-port rotary valve 152 comprises an inlet passageway 162 that is in open communication with an inlet port 164 and an outlet passageway 166 that is in open communication with an outlet port 168 such that rotatable valve member 154 can be rotated by a valve motor 170 operatively coupled thereto for selectively communicating the rotatable passageway 156 between the stationary passageway 158 in open communication with the chamber 22 and either the inlet port 164 or the outlet port 168 of the valve 152 as will be further delineated hereinbelow.

Figure 8:
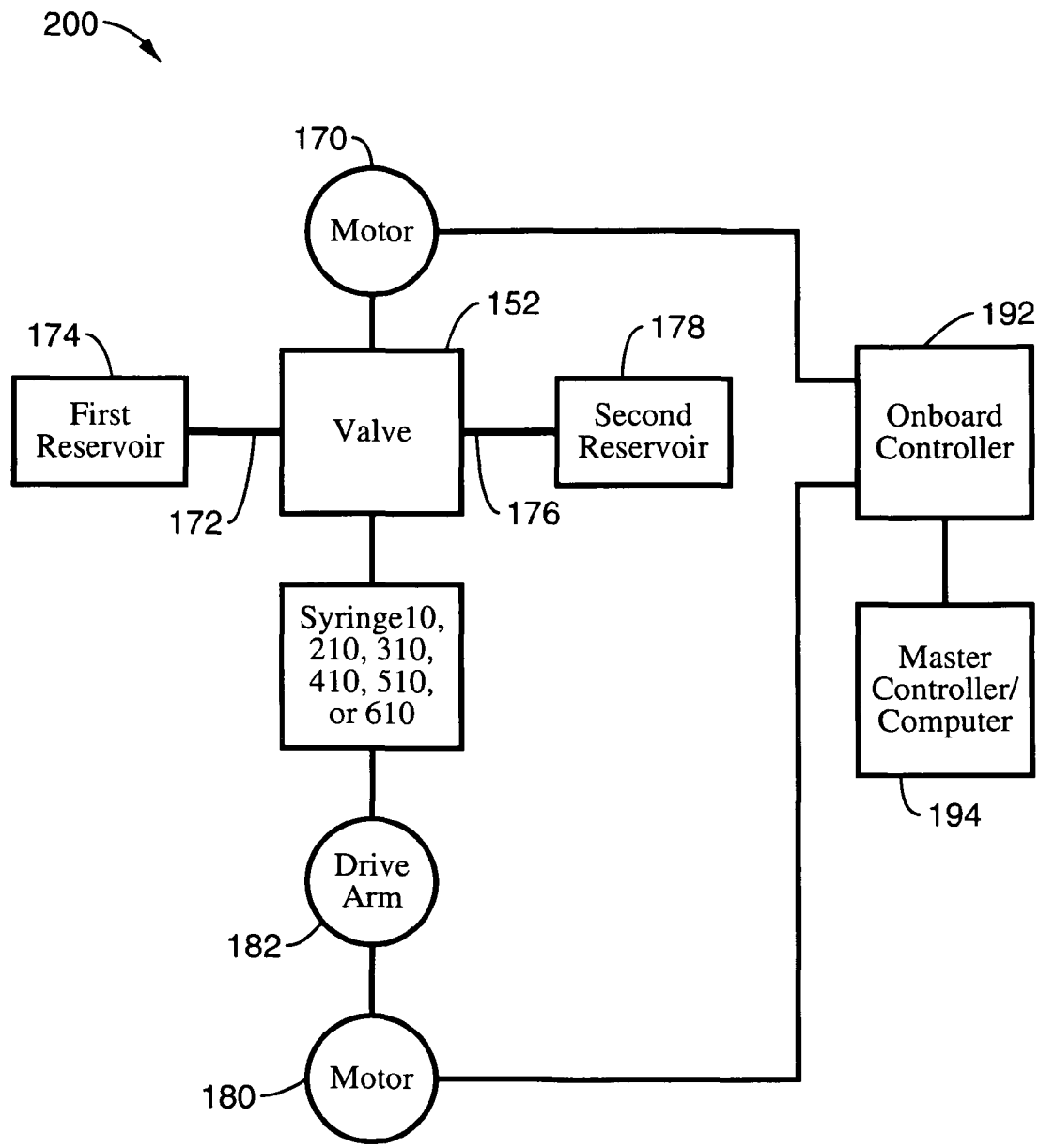
FIG. 8 is a block diagram view of a syringe pump system comprising an embodiment of a negative dead volume syringe.

As illustrated in FIG. 8, an inlet fluid line 172 typically couples the inlet port 164 to a first reservoir 174 of fluid while an outlet fluid line 176 typically couples the outlet port 168 to a second reservoir 178 for dispensing fluid thereto as will be further delineated hereinbelow.

Referring to FIGS. 7 and 8, the syringe pump 150 further comprises a plunger drive motor 180 operatively coupled to a linearly reciprocable drive arm 182 which, in turn, is coupled to the drive head 70 of the plunger rod 64 by way of a thumb screw 184 comprised of a knurled head 186 transitioning into a threaded shaft 188 passing through an aperture 190 disposed in the drive arm 182 and threadedly coupling with the internally threaded sleeve 76 disposed within the plunger rod 64 thereby coupling the linearly reciprocable plunger 62 and therefore the plunger tip 102 to the linearly reciprocable drive arm 182 in an easily detachable and linearly reciprocable manner.

In one embodiment, the valve motor 170 and the plunger drive motor 180 are electrically or electromagnetically coupled to and controlled by a onboard controller 192 which, in turn, is electrically or electromagnetically coupled to a master controller or computer 194 for communicating with the controller 192 for providing programmable orchestration of syringe pump operation.

Use and Operation

In use and operation, and referring to the drawings, the negative dead volume syringe 10 is coupled between, and in operative engagement with, the multi port rotary valve 152 and the linearly reciprocable drive arm 182 of the syringe pump 150 are both electrically or electromagnetically coupled to the onboard controller 192 which, in turn, is electrically or electromagnetically coupled to the master controller or computer 194 thereby defining a syringe pump system 200. The first reservoir 174 of fluid is coupled to inlet port 164 of the valve 152 via the inlet fluid line 172 and the second reservoir 178, or a subsequent syringe pump system, is coupled to the outlet port 168 of the valve 152 via the outlet fluid line 176. The syringe pump system 200 is then booted up such that the master controller or computer 194 can send electrical or electromagnetic signals to and/or receive electrical or electromagnetic signals from the onboard controller 192.

The controllers 192, 194 then control the operation of the valve motor 170 and the plunger drive motor 180 for selectively rotating the rotatable valve member 154 and proximately or distally driving the linearly reciprocable drive arm 182 for precisely and accurately aspirating and dispensing fluids.

For example, and during a general aspiration stroke, the controllers 192, 194 control the operation of the valve motor 170 for rotating the rotatable valve member to communicate the inlet port 164 with the stationary passageway or dead volume 158. Additionally, the controllers 192, 194 control the operation of the plunger drive motor 180 for driving the linearly reciprocable drive arm 182 to proximally drive the plunger tip 102 within the chamber 22 of the syringe 10 such that fluid is aspirated into the chamber 22 of the syringe 10 by flowing through the inlet fluid line 172, the inlet port 164, the inlet passageway 162, the rotatable passageway 156, the stationary passageway or dead volume 158, and the tip passageway 46 to the chamber 22 of the syringe 10.

During a general dispensing stroke, the controllers 192, 194 control the operation of the valve motor 170 for rotating the rotatable valve member 154 to communicate the outlet port 168 with the stationary passageway or dead volume 158. Additionally, the controllers 192, 194 control the operation of the plunger drive motor 180 for driving the linearly reciprocable drive arm 182 to distally drive the plunger tip 102 within the chamber 22 of the syringe 10 such that fluid is dispensed from the chamber 22 of the syringe 10 through the tip passageway 46, the stationary passageway or dead volume 158, the rotatable passageway 156, the outlet passageway 166, the outlet port 168, and the outlet fluid line 176 to the second reservoir 178 or, perhaps to a second syringe pump system 200.

More specifically, and during use and operation, each syringe pump system 200 typically undergoes an initialization process for priming the system with one or more user selected fluids. When the fluid first reaches the valve, the syringe 10 draws in both fluid and air causing the fluid to foam or froth within the chamber 22 of the syringe. Then, the rotatable valve member 154 is turned and the plunger 62 is actuated to dispense or push the fluid and air out of the outlet port 168 of the valve 152.

During this process, the proximal plunger tip portion 104 provides a tight, leak-free seal between the plunger tip 102 and the chamber 22, the frusto-conically shaped medial plunger tip portion 124 slideably and conformingly engages the frusto-conically shaped passageway 46 of the syringe tip 32, and the distal plunger tip extension or nubbin 134 extends beyond the sealing surface 42 of the syringe tip 32 and is complementally received within and substantially or completely fills the valve dead volume 158 of the multi-port rotary valve 152 so that the plunger tip 102 ensures complete or substantially complete dispensing of fluid while reducing bubble formation and facilitating bubble removal from the chamber 22, from the passageway 46 of the syringe tip 32, and from the valve dead volume 158 upon full distal displacement of the elongated plunger rod thereby ameliorating or overcoming air being trapped within the valve dead volume 158 and being drawn back into the syringe 10 ahead of the inflowing fluid during the next aspiration stroke.

Hence, the negative dead volume syringe 10 removes the dead volume from or provides zero dead volume in the chamber 22 and tip 32 of the syringe 10 and subtracts or displaces dead volume 158 from the syringe valve 152 coupled to the syringe 10 resulting both in quicker priming times by requiring fewer priming strokes and in less working fluid loss as compared to a conventional syringe pump system.

Additionally, and during use and operation, the syringe pump system 200 may require purging of the syringe pump system 200 for changing from, for example, a first fluid to a second different fluid.

During this process, the negative dead volume syringe 10 of the syringe pump system 200 aspirates or draws in both the first fluid and the second different fluid into the syringe chamber 22 where the fluids mix. Subsequently, this fluid mixture is dispensed out of the syringe 10 by rotating the rotatable valve member 154 to communicate the syringe chamber 22 with the outlet port 168 of the valve 152 and then actuating the plunger 62 for dispensing the fluid mixture out of the outlet port 168.

During this dispensing stroke, the proximal plunger tip portion 104 provides a tight, leak-free seal between the plunger tip 102 and the chamber 22, the frusto-conically shaped medial plunger tip portion 124 slideably and conformingly engages the frusto-conically shaped passageway 46 of the syringe tip 32, and the distal plunger tip extension or nubbin 134 extends beyond the sealing surface 42 of the syringe tip 32 and is complementally received within and substantially or completely fills the valve dead volume defined by the stationary passageway 158 of the multi-port rotary valve 152 so that the plunger tip 102 ensures complete or substantially complete dispensing of fluid from the chamber 22, from the passageway 46 of the syringe tip 32, and from the valve dead volume 158 upon full distal displacement of the elongated plunger rod thereby ameliorating or overcoming a portion of the fluid mixture from remaining within the dead volume 158 of the valve 152 and being drawn back into the chamber 22 of the syringe on the next aspiration stroke which, heretofore, resulted a diminishing return or dilution of the fluid drawn from the inlet fluid line.

Hence, the distal plunger tip extension or nubbin 134 of negative dead volume syringe 10 subtracts or displaces the dead volume 158 from the syringe valve 152 thereby clearing out fluid mixtures from this dead volume on each dispensing stroke so that the fluid mixture is not drawn back into the syringe thereby eliminating the known prior art problem of the diminishing return or dilution over time on subsequent aspiration strokes and thus, decreasing the number of strokes, the time, the wasted fluid, and the associated costs required to purge one fluid when changing over to another.

Furthermore, and during use and operation, the syringe pump system 200 often handles a fluid that has a small amount of gas that can degas and turn into bubbles because, by its nature, the plunger 62 in the syringe 10 is reducing and pressurizing the fluid. When the pressure on the fluid is reduced, the bubbles out gas and turn into bubbles which are substantially or completely removed from the syringe 10 and syringe valve 152 by the proximal plunger tip portion 104 providing a tight, leak-free seal between the plunger tip 102 and the chamber 22, the frusto-conically shaped medial plunger tip portion 124 slideably and conformingly engaging the frusto-conically shaped passageway 46 of the syringe tip 32, and the distal plunger tip extension or nubbin 134 extending beyond the sealing surface 42 of the syringe tip 32 and being complementally received within and substantially or completely filling the valve dead volume 158 of the valve 152 such that the plunger tip 102 facilitates bubble removal from the chamber 22, from the passageway 46 of the syringe tip 32, and from the valve dead volume 158 of the valve 152 upon full distal displacement of the elongated plunger rod thereby ameliorating or overcoming the known prior art problem of bubbles tending to stay in the syringe 22 or dead volume 158 of the valve 152 and stubbornly stick to the sides thereof such that an air spring is created that degrades accuracy.

Moreover, and in use and operation, the negative dead volume syringe 10 can be coupled in a vertical, horizontal, or oblique orientation to a variety of different syringe pumps at a location between, and in operative engagement with, a variety of different drives means employing different methods for driving the plunger and a variety of different valves employing different methods for switching or opening and closing flow paths inside of the valve by means other than a rotary action.

Additional Embodiments

Figure 9:
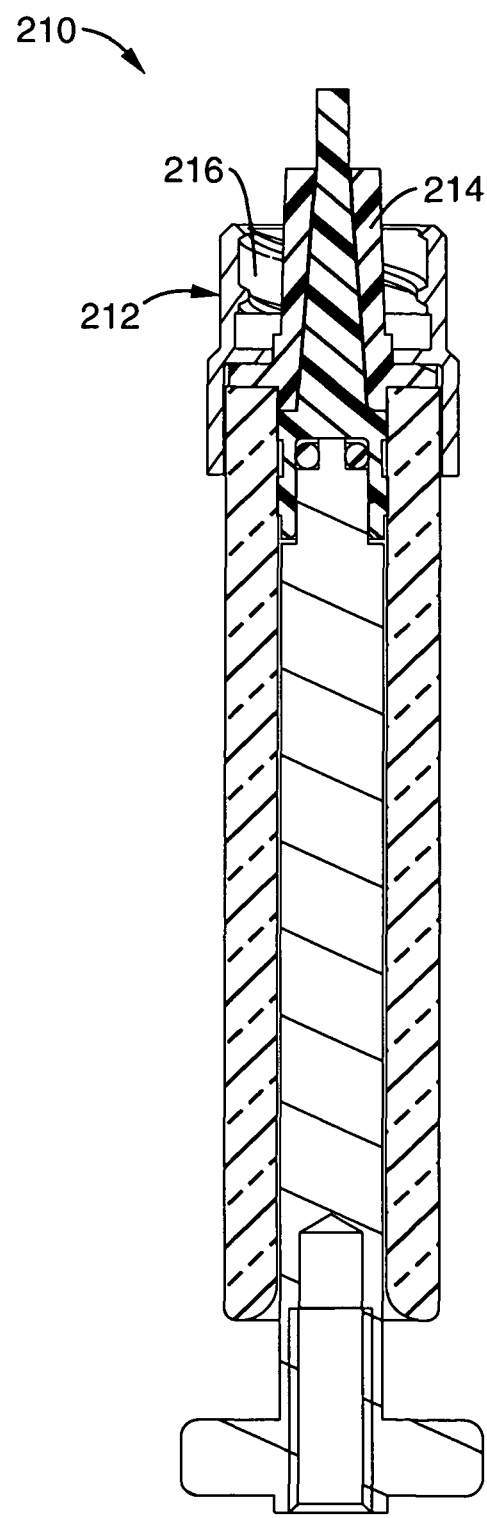
FIG. 9 is a sectional view of another embodiment of a negative dead volume syringe.
Figure 10:
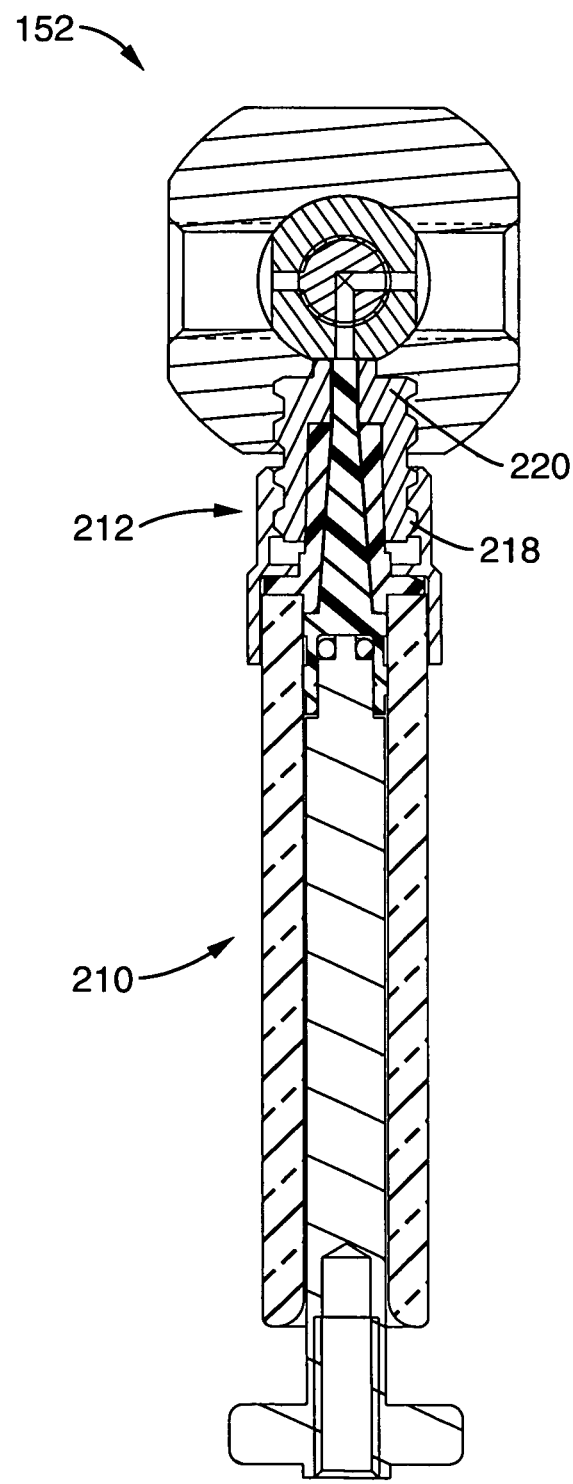
FIG. 10 is a sectional view of the negative dead volume syringe illustrated in FIG. 9 coupled to the multi-port rotary valve illustrated in FIG. 5.

In another embodiment, and referring to FIGS. 9 and 10, the negative dead volume syringe 10 is illustrated with an alternative syringe/valve coupling means for defining a negative dead volume syringe 210. More specifically, the negative dead volume syringe 210 employs a syringe/valve coupling means comprised of a conventional locking luer-type collar 212 concentrically surrounding a syringe tip or insert 214 wherein the locking luer-type collar 212 has internally threaded section 216 coupling with externally threaded section 218 of adaptor 220 fitted to the syringe receiving port 160 of the multi port rotary valve 152.

A variety of other conventional coupling means may also be employed for releasably attaching the distal end of the negative dead volume syringe to at least one of the large variety of conventional valves which, as noted hereinabove, are exemplified by the valves available from the assignee of the present patent application.

The use and operation of the negative dead volume syringe 210 follows the use and operation of the negative dead volume syringe 10 delineated in detail hereinabove.

Figure 11:
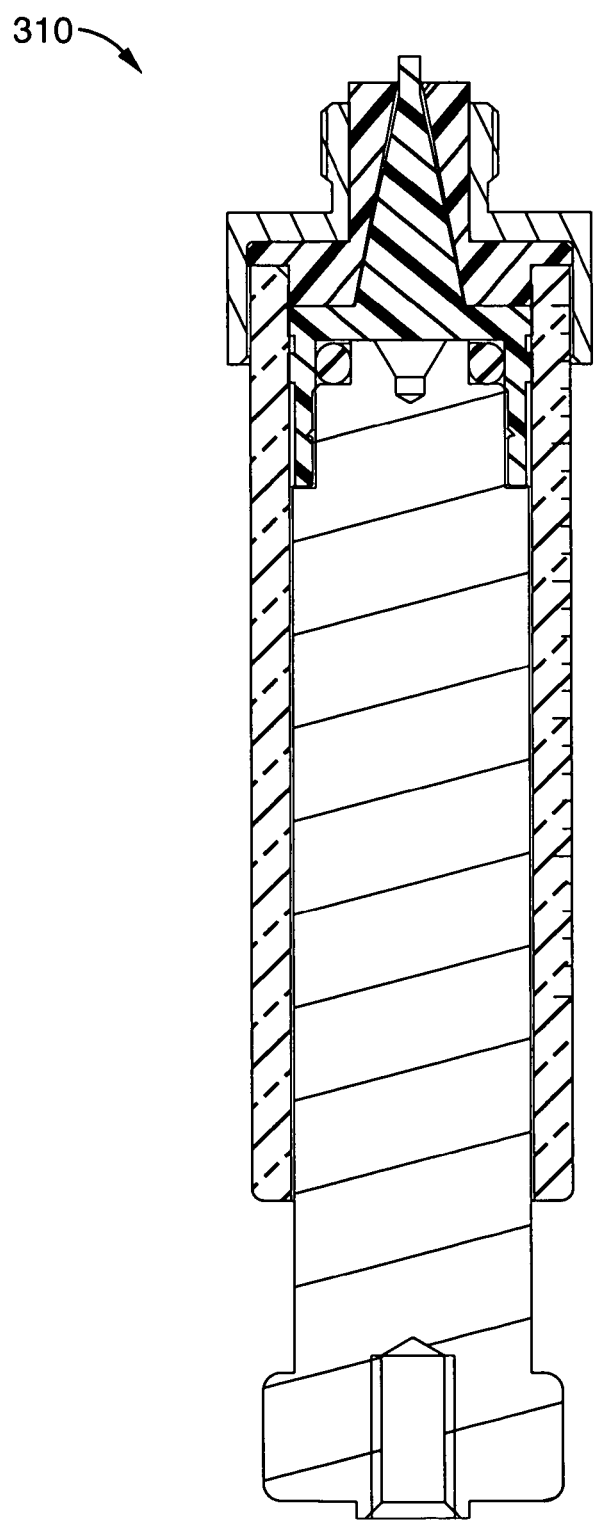
FIG. 11 is a sectional view of another embodiment of a negative dead volume syringe.

In another embodiment, FIG. 11 illustrates a negative dead volume syringe 310 comprised of parts sized to accommodate a larger diameter chamber size as compared to negative dead volume syringe 10.

The use and operation of the negative dead volume syringe 310 follows the use and operation of the negative dead volume syringe 10 delineated in detail hereinabove.

Figure 12:
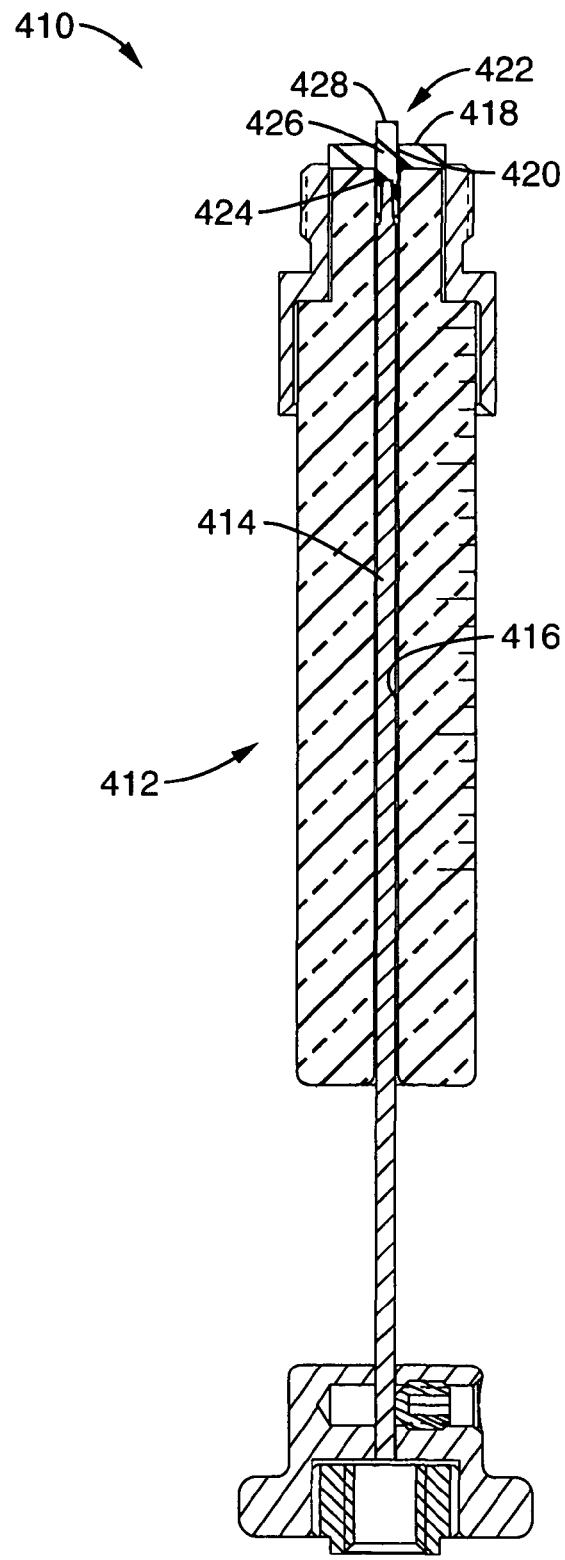
FIG. 12 is a sectional view of another embodiment of a negative dead volume syringe.

In another embodiment, and referring to FIG. 12, a negative dead volume syringe 410 comprised of a thick walled barrel 412 and parts sized to accommodate a smaller diameter chamber size as compared to negative dead volume syringe 10.

Particularly, a plunger rod 414 of syringe 410 has been reduced in diameter as compared to plunger rod 64 of syringe 10 to accommodate a reduced diameter chamber 416 of the thick walled barrel 412 of syringe 410 as compared to chamber 22 of syringe 10. Additionally, a syringe tip 418 is adhesively coupled to a distal end of the thick walled barrel 412 and includes a cylindrically shaped or slightly distally tapering syringe tip passageway 420 extending therethrough in open communication with the chamber 416.

Furthermore, a plunger tip 422 is provided which comprises: a cylindrical or slightly tapering proximal plunger tip portion 424 coupled to the distal end of the plunger rod 414; a cylindrical or slightly tapering medial plunger tip portion 426 distally extending from the proximal plunger tip portion 424 and shaped complemental to the syringe tip passageway 420; and a cylindrical or slightly tapering distal plunger tip extension or nubbin 428 sized to extend beyond the syringe tip passageway 420 and shaped to be complementally received within and substantially fill a valve dead volume defined by a stationary passageway of a rotary valve as delineated hereinabove so that the plunger tip 422 ensures complete or substantially complete dispensing of fluid from the chamber 416 while reducing bubble formation and facilitating bubble removal from the chamber 416, from the syringe tip passageway 420, and from the valve dead volume upon full distal displacement of the elongated plunger rod 414 and the plunger tip 422 coupled thereto.

The use and operation of the negative dead volume syringe 410 follows the use and operation of the negative dead volume syringe 10 delineated in detail hereinabove.

Figure 13:
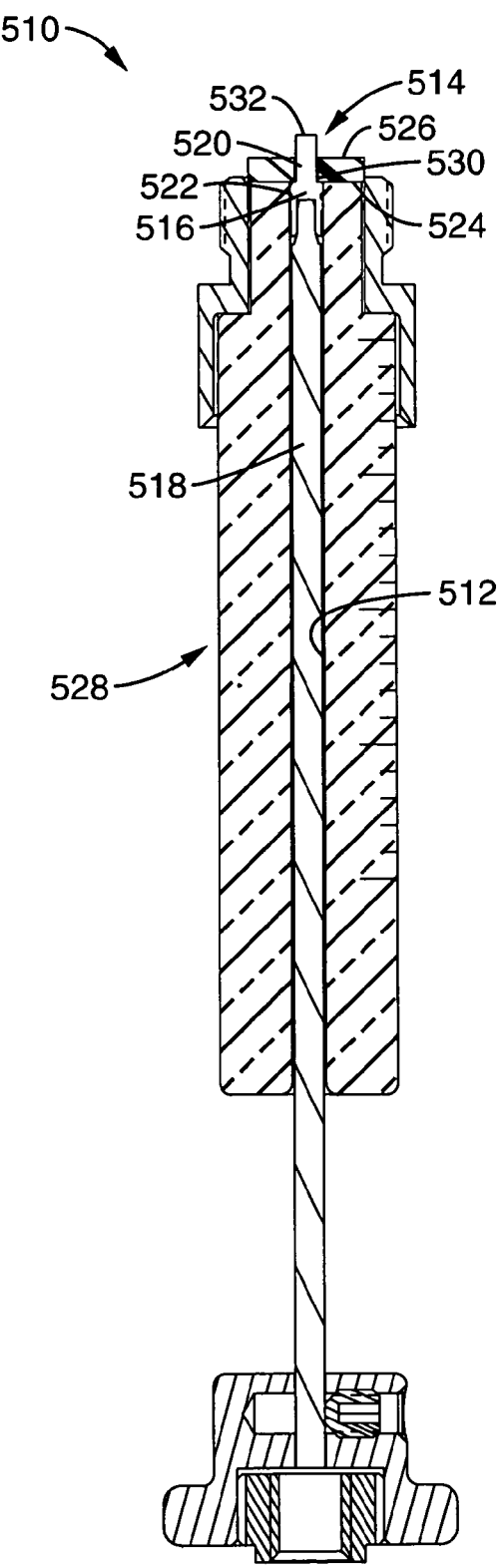
FIG. 13 is a sectional view of another embodiment of a negative dead volume syringe.

In another embodiment, and referring to FIGS. 13, a negative dead volume syringe 510 is illustrated similar to syringe 410, but comprising a lager diameter chamber 512 and a variation in a plunger tip 514.

Specifically, the plunger tip 514 comprises a cylindrical or slightly tapering proximal plunger tip portion 516 coupled to the distal end of an elongated plunger rod 518.

The plunger tip 514 further comprises a cylindrical or slightly tapering medial plunger tip portion 520 distally extending from and having a diameter less than a diameter of the proximal plunger tip portion 516 thereby defining a shoulder 522 which is shaped to abut and seal against an annular rear face 524 of a syringe tip 526 adhesively coupled to a distal end of a thick walled barrel 528 of the syringe 510. The syringe tip 526 includes a syringe tip passageway 530 shaped complemental to the shape of medial plunger tip portion 520 for complementally receiving the medial plunger tip portion 520 therein.

The plunger tip 514 further comprises a cylindrical or slightly tapering distal plunger tip extension or nubbin 532 sized to extend beyond the syringe tip passageway 530 and shaped to be complementally received within and substantially fill a valve dead volume defined by a stationary passageway of a conventional rotary valve so that the plunger tip 514 ensures complete or substantially complete dispensing of fluid from the chamber 512 of the thick walled barrel 528 of the syringe while reducing bubble formation and facilitating bubble removal from the chamber 512, from the syringe tip passageway 530, and from the valve dead volume upon full distal displacement of the elongated plunger rod 518 and the plunger tip 514 coupled thereto.

The use and operation of the negative dead volume syringe 510 follows the use and operation of the negative dead volume syringe 10 delineated in detail hereinabove.

Figure 14:
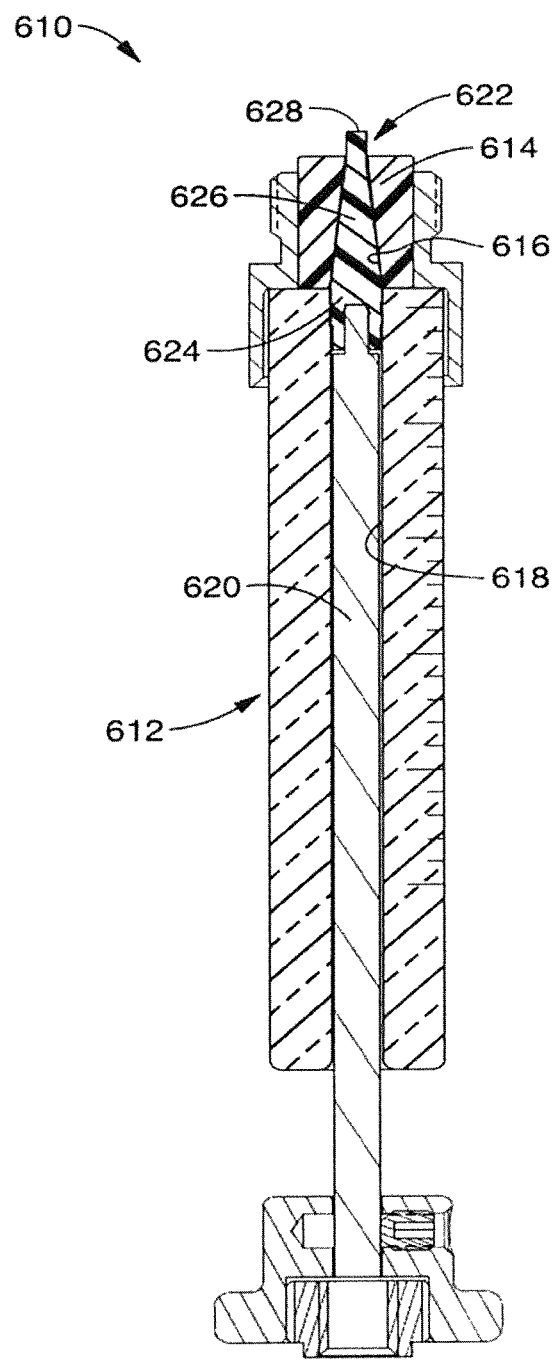
FIG. 14 is a sectional view of another embodiment of a negative dead volume syringe.

In another embodiment, FIG. 14 illustrates a negative dead volume syringe 610 comprised of a thick walled barrel 612 and a syringe tip 614 adhesively coupled to a distal end of the thick walled barrel 612 and including a frusto-conically shaped or distally tapering syringe tip passageway 616 extending therethrough in open communication with a chamber 618 of the thick walled barrel 612.

Additionally, the negative dead volume syringe 610 further comprises a plunger tip 622 comprising: a cylindrical proximal plunger tip portion 624 coupled to a distal end of an elongated plunger rod 620; a frusto-conically shaped medial plunger tip portion 626 distally extending from the proximal plunger tip portion 624 and shaped complemental to the frusto-conically shaped syringe tip passageway 616; and a cylindrical or slightly tapering distal plunger tip extension or nubbin 628 sized to extend beyond the syringe tip passageway 616 and shaped to be complementally received within and substantially fill a valve dead volume defined by a stationary passageway of a rotary valve so that the plunger tip 622 ensures complete or substantially complete dispensing of fluid while reducing bubble formation and facilitating bubble removal from the chamber 618, from the syringe tip passageway 616, and from the valve dead volume upon full distal displacement of the elongated plunger rod 620 and the plunger tip 622 coupled thereto.

The use and operation of the negative dead volume syringe 610 follows the use and operation of the negative dead volume syringe 10 delineated in detail hereinabove.

Accordingly, it should be apparent that further numerous structural modifications and adaptations may be resorted to without departing from the scope and fair meaning of the present invention as set forth hereinabove and as described herein below by the claims.

We claim:

1. A syringe plunger tip for a syringe, said syringe plunger tip comprising:
    a proximal plunger tip portion coupled to a plunger rod drivable to distally and proximally slide said proximal plunger tip portion within a chamber of a body of a syringe, the chamber being defined by an interior of a sidewall of the body of the syringe, said sidewall axially-extending between an open distal end and an open proximal end of the body of the syringe;

a medial plunger tip portion coupled to and slideable with said proximal plunger tip portion, said medial plunger tip portion shaped complemental to an open ended passageway defined by an internal sidewall of a syringe tip coupled to the open distal end of the body of the syringe;

a plunger tip extension coupled to and slideable with said medial plunger tip portion;

said plunger tip extension having a solid cross sectional area extending from a bottom portion of said plunger tip extension adjacent said medial portion to a substantially flat apex portion of said plunger tip extension;

said plunger tip extension distally extending from said medial plunger tip portion and sized to pass through and extend beyond the open ended passageway of the syringe tip;

a valve having a passageway defining a deal volume of said valve and defined by an internal sidewall of the valve coupleable to the syringe tip; and said plunger tip extension shaped to be complementally received within said passageway defining said dead volume of said valve and defined by said internal sidewall of said valve coupleable to the syringe tip for substantially displacing fluid and air from said dead volume of said valve.

2. The syringe plunger tip of claim 1 wherein said proximal plunger tip portion, said medial plunger tip portion, and said plunger tip extension are a single monolith of material.

3. The syringe plunger tip of claim 1 wherein said proximal plunger tip portion and said medial plunger tip portion are a single monolith of material and said plunger tip extension is a separate monolith of material operatively coupled to said medial portion.

4. The syringe plunger tip of claim 1 wherein said plunger tip extension and said medial plunger tip portion are a single monolith of material and said proximal plunger tip portion is a separate monolith of material operatively coupled to said medial portion.

5. The syringe plunger tip of claim 1 wherein said plunger tip extension, said medial plunger tip portion, and said proximal plunger tip portion are each separate monoliths of material with said plunger tip extension operatively coupled to said medial plunger tip portion and said medial plunger tip portion operatively coupled to said proximal plunger tip portion.

6. The syringe plunger tip of claim 1 wherein said proximal plunger tip portion, said medial plunger tip portion, and said plunger tip extension are formed from a polytetrafluoroethylene (PTFE) material.

7. The syringe plunger tip of claim 1 wherein said proximal plunger tip portion, said medial plunger tip portion, and said plunger tip extension are formed from an ultra-high molecular weight polyethylene (UHM.WPE) material.

8. The syringe plunger tip of claim 1 wherein said plunger tip extension is formed from a different material than said proximal and medial plunger tip portions.

9. The syringe plunger tip of claim 1 wherein said proximal plunger tip portion is cylindrically shaped.

10. The syringe plunger tip of claim 1 wherein said medial plunger tip portion is frusta-conically shaped.

11. The syringe plunger tip of claim 1 wherein said plunger tip extension is cylindrically shaped.

12. The syringe plunger tip of claim 1 wherein said medial plunger tip portion is cylindrically shaped.

13. The syringe plunger tip of claim 1 wherein said plunger tip extension is slightly distally tapered.

14. The syringe plunger tip of claim 1 wherein said proximal plunger tip portion includes at least one seal disposed on an exterior surface thereof for providing a tight, leak-free seal between the plunger tip and the interior of the sidewall of the body of the syringe.

15. The syringe plunger tip of claim 1 wherein said proximal plunger tip portion includes a plurality of spaced apart collocated seals disposed on an exterior surface thereof for providing a tight, leak-free seal between the plunger tip and the interior of the sidewall of the body of the syringe.

16. A syringe, comprising:
a syringe body comprised of cylindrical sidewall axially-extending between an open distal end and an open proximal end, said cylindrical sidewall having an interior surface defining a chamber for retaining fluid;

a syringe tip coupled to said open distal end of said syringe body, said syringe tip having a open ended passageway extending therethrough, said open ended passageway defined by an interior surface of said syringe tip axially extending between a back opening and a front opening of said syringe tip, said open ended passageway being axially aligned with and in open communication with said chamber of said syringe body;

a plunger rod having a first end portion and a second end portion wherein said second end portion is disposed outside of said syringe body for being drivable to linearly driving said first end portion of said plunger rod distally and proximally within said chamber of said syringe body;

a valve having a passageway defining a dead volume of said valve and defined by an internal sidewall of the valve coupleable to the syringe tip; and a plunger tip comprising:
a proximal portion coupled to said first end portion of said plunger rod;
a medial portion coupled to said proximal portion, said medial portion shaped to be complementally received within and substantially fill said open ended passageway of said syringe tip for displacing fluid and air therefrom; and
a plunger tip extension coupled to and reciprocable with said medial portion, said plunger tip extension having a said plunger tip extension having a solid cross sectional area extending from a bottom portion of said plunger tip extension adjacent said medial portion to a substantially flat apex portion of said plunger tip extension, said plunger tip extension distally extending from said medial plunger tip portion and sized to pass through and extend distally beyond the open ended passageway of said syringe tip and shaped to be complementally received within said passageway of said valve defining said dead volume and defined by said internal sidewall of said valve coupleable to said syringe tip for substantially displacing fluid and air from said dead volume of said valve wherein at least a portion of the air displaced from said dead volume of said valve is retained in a thin film of fluid inflated by the air thereby defining an air bubble.

17. The syringe of claim 16 wherein said proximal portion of said plunger tip is cylindrically shaped.

18. The syringe of claim 17 wherein said open ended passageway of said syringe tip is frusta-conically shaped and defined by a frusta-conically shaped interior surface of said syringe tip extending between and tapering from said back opening and said front opening of said syringe tip.

19. The syringe of claim 18 wherein said medial portion of said plunger tip includes a continuous frusta-conically shaped cross-sectional area having a fiesta-conically shaped outer surface shaped complemental to said frusta-conically shaped interior surface of said syringe tip for being complementally received within and substantially filling said open ended passageway of said syringe tip for displacing fluid and air therefrom.

20. The syringe of claim 19 wherein said plunger tip extension of said plunger tip is cylindrically shaped.

21. The syringe of claim 19 wherein said plunger tip extension of said plunger tip is slightly distally tapered.

22. The syringe of claim 17 wherein said open ended passageway of said syringe tip is cylindrically shaped and defined by a cylindrically shaped interior surface of said syringe tip extending between said back opening and said front opening of said syringe tip.

23. The syringe of claim 22 wherein said medial portion of said plunger tip includes a continuous cylindrically shaped cross-sectional area having a cylindrically shaped outer surface shaped complemental to said cylindrically shaped interior surface of said syringe tip for being complementally received within and substantially filling said open ended passageway of said syringe tip for displacing fluid and air therefrom.

24. The syringe of claim 23 wherein said plunger tip extension of said plunger tip is cylindrically shaped.

25. The syringe of claim 23 wherein said plunger tip extension of said plunger tip is distally tapered.

26. A syringe pump system, comprising:
a syringe body comprised of cylindrical sidewall axially-extending between an open distal end and an open proximal end, said cylindrical sidewall having an interior surface defining a chamber for retaining fluid;
a syringe tip coupled to said open distal end of said syringe body, said syringe tip having an open ended passageway extending therethrough, said open ended passageway defined by an interior surface of said syringe tip axially extending between a back opening and a front opening of said syringe tip, said open ended passageway being axially aligned with and in open communication with said chamber of said syringe body;
a valve comprising an inlet port, an outlet port, a valve passageway coupled to said syringe tip and defined by an internal sidewall of the valve and defining a dead volume in open communication with said open ended passageway of said syringe tip and said chamber of said syringe body, and a rotatable member having a rotatable passageway extending therethrough wherein said rotatable member is selectively rotatable for aligning said rotatable passageway to provide open communication between said inlet port and said valve passageway defining said dead volume or for aligning said rotatable passageway to provide open communication between said valve passageway defining said dead volume and said outlet port;
a plunger rod having a first end portion and a second end portion wherein said second end portion is disposed outside of said chamber and said first end portion is disposed within said chamber;
a drive means operatively coupled to said second end portion of said plunger rod for linearly driving said first end portion of said plunger rod distally and proximally within said chamber; and
a plunger tip comprising:
a proximal portion coupled to said first end portion of said plunger rod;
a medial portion coupled to said proximal portion, said medial portion shaped to be complementally received within and substantially fill said open ended passageway of said syringe tip for displacing fluid and air therefrom; and
a plunger tip extension coupled to said medial portion, said plunger tip extension having a solid cross sectional area extending from a bottom portion of said plunger tip extension adjacent said medial portion to a substantially flat apex portion of said plunger tip extension, said plunger tip extension distally extending from said medial portion and sized to pass through and extend distally beyond said open ended passageway of said syringe tip and shaped to be complementally received within said passageway of said valve for substantially filling said dead volume of said valve for forcing fluid and existing air out of said dead volume when said plunger tip extension is driven into said passageway of said valve by said drive means distally driving said plunger rod.

27. The syringe pump system of claim 26 wherein said proximal portion of said plunger tip is cylindrically shaped.

28. The syringe pump system of claim 27 wherein said open ended passageway of said syringe tip is frusta-conically shaped and defined by a frusta-conically shaped interior surface of said syringe tip extending between and tapering from said back opening and said front opening of said syringe tip.

29. The syringe pump system of claim 28 wherein said medial portion of said plunger tip includes a continuous frusta-conically shaped cross-sectional area having a frusta-conically shaped outer surface shaped complemental to said frusta-conically shaped interior surface of said syringe tip for being complementally received within and substantially filling said open ended passageway of said syringe tip for displacing fluid and air therefrom.

30. The syringe pump system of claim 29 wherein said plunger tip extension of said plunger tip is cylindrically shaped.

31. The syringe pump system of claim 29 wherein said plunger tip extension of said plunger tip is slightly distally tapered.

32. The syringe pump system of claim 27 wherein said open ended passageway of said syringe tip is cylindrically shaped and defined by a cylindrically shaped interior surface of said syringe tip extending between said back opening and said front opening of said syringe tip.

33. The syringe pump system of claim 32 wherein said medial portion of said plunger tip includes a continuous cylindrically shaped cross-sectional area having a cylindrically shaped outer surface shaped complemental to said cylindrically shaped interior surface of said syringe tip for being complementally received within and substantially filling said open ended passageway of said syringe tip for displacing fluid and air therefrom.

34. The syringe pump system of claim 33 wherein said plunger tip extension of said plunger tip is cylindrically shaped.

35. The syringe pump system of claim 33 wherein said plunger tip extension of said plunger tip is distally tapered.

* * * * *